(12) United States Patent
Jayasinghe et al.

(10) Patent No.: US 11,844,863 B2
(45) Date of Patent: Dec. 19, 2023

(54) ORAL DELIVERY SYSTEM FOR BIOACTIVE AGENTS

(71) Applicant: EWOS INNOVATION AS, Dirdal (NO)

(72) Inventors: Suwan Nalin Jayasinghe, London (GB); Goran Klaric, Dirdal (NO); Simon Wadsworth, Harstad (NO)

(73) Assignee: EWOS INNOVATION AS, Dirdal (NO)

( * ) Notice: Subject to any disclaimer, the term of this patent is extended or adjusted under 35 U.S.C. 154(b) by 0 days.

(21) Appl. No.: 17/929,556

(22) Filed: Sep. 2, 2022

(65) Prior Publication Data

US 2022/0409541 A1    Dec. 29, 2022

Related U.S. Application Data

(63) Continuation of application No. 15/579,466, filed as application No. PCT/NO2016/050113 on Jun. 2, 2016, now abandoned.

(30) Foreign Application Priority Data

Jun. 3, 2015 (GB) .................................. 1509608
Jun. 3, 2015 (NO) .................................. 20150715

(51) Int. Cl.
*A61K 47/36*    (2006.01)
*A61K 9/16*    (2006.01)
(Continued)

(52) U.S. Cl.
CPC .......... *A61K 9/1652* (2013.01); *A23K 20/163* (2016.05); *A23K 50/80* (2016.05);
(Continued)

(58) Field of Classification Search
CPC .... A61K 50/80; A61K 9/1652; A61K 9/5036; A61K 38/44; A61K 47/36
See application file for complete search history.

(56) References Cited

U.S. PATENT DOCUMENTS

| | | |
|---|---|---|
| 4,935,250 A | 6/1990 | Cox |
| 5,622,718 A | 4/1997 | Al-Shamkhani |

(Continued)

FOREIGN PATENT DOCUMENTS

| | | |
|---|---|---|
| CN | 1124584 A | 6/1996 |
| CN | 1599564 A | 3/2005 |

(Continued)

OTHER PUBLICATIONS

Bucking, C. and Wood, C. M. 2009. The effect of postprandial changes in pH along the gastro-intestinal tract on the distribution of ions ?etween the solid and fluid phases of the chyme in rainbow trout. Aquaculture Nutrition, vol. 15, Issue 3, pp. 282-296.

(Continued)

*Primary Examiner* — Johann R Richter
*Assistant Examiner* — Danielle Sullivan

(57) ABSTRACT

The present invention relates to a functional feed and an oral delivery system for delivery of bioactive macromolecules. The oral delivery system comprises ethylenediammonium alginate which is a vehicle for delivery of macromolecular drugs. The oral delivery system according to the present invention is particularly suitable for use in combination with functional feeds in fish.

9 Claims, 3 Drawing Sheets

Figure 1:
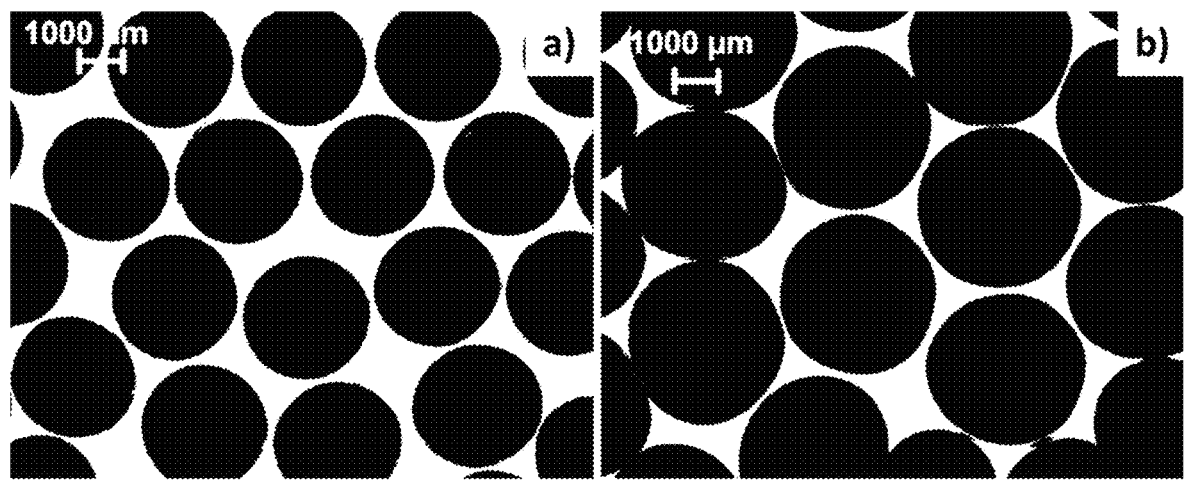

(51) Int. Cl.
*A61K 9/50* (2006.01)
*A23K 20/163* (2016.01)
*A23K 50/80* (2016.01)
*A61K 38/44* (2006.01)

(52) U.S. Cl.
CPC ............ *A61K 9/5036* (2013.01); *A61K 38/44* (2013.01); *A61K 47/36* (2013.01)

(56) References Cited

U.S. PATENT DOCUMENTS

| | | | |
|---|---|---|---|
| 7,014,845 B1 | 3/2006 | Labarre | |
| 2005/0037081 A1 | 2/2005 | Eccleston | |
| 2013/0129865 A1 | 5/2013 | Goold | |

FOREIGN PATENT DOCUMENTS

| | | |
|---|---|---|
| CN | 1618434 A | 5/2005 |
| CN | 101365427 A | 2/2009 |
| CN | 101549158 A | 10/2009 |
| CN | 103627010 A | 3/2014 |
| EP | 0712635 B1 | 5/2003 |
| JP | 2001233786 A | 8/2001 |
| WO | 9528227 W | 10/1995 |
| WO | 03026489 W | 4/2003 |
| WO | 2004043140 A2 | 5/2004 |
| WO | 2005115341 W | 12/2005 |
| WO | 2013187852 A1 | 12/2013 |

OTHER PUBLICATIONS

Cooper R. et al. "Molecular Size and Shape of the Ethylenediammonium Salt of a Polycarboxylic Acid", J. Chem. Soc. (resumed) 1962, 2705-2708.
Feenstra, T.P., De Bruyn, P.L., 1979. Formation of calcium phosphates in moderately supersaturated solutions. J. Phys. Chem. 83, 475-479.
International Search Report of PCT/NO2016/050113 dated Nov. 16, 2016 (5 pgs).
Kim, C. and Lee, E., 1992. The controlled release of blue dextran from alginate beads. Int. J. Pharm. 79, 11-19.
Kuen Yong Lee et al. "Alginate: Properties and biomedical Applications", Progress in Polymer Science, 37 (2012), p. 106-126, Pergamon Press, Oxford, GB, ISSN 0079-6700.
Li, Zhi-Yong et al. "Preparation and studies of alginate covalently cross-linked hydrogels", Guangpu Shiyanshi (2008), 25(5), abstract, ISSN: 1004-8138.
Lihan Chen et al: "Augmentation of the Antibody Response of Atlantic Salmon by Oral Administration of Alginate-Encapsulated IPNV Antigens", PLOS ONE, vol. 9, No. 10, Oct. 13, 2014 (Oct. 13, 2014), pp. e109337, XP055303682, DOI:10.1371/journal.pone. 0109337.
Masao Tanihara et al.: "Sustained release of basic fibroblast growth factor and angiogenesis in a novel covalently crosslinked gel of heparin and alginate", Journal of Biomedical Materials Research, vol. 56, No. 2, Jan. 1, 2001 (Jan. 1, 2001) pp. 216-221, XP055303920, US, ISSN: 0021/9304, DOI:10.1002/1097-4636 (200108)56:2<216::AID-JBM1086>3.0.CO;2-N.
Maurice S et al: "Oral immunization of Carassius auratus with modified recombinant A-layer proteins entrapped in alginate beads", Vaccine, Elsevier Ltd, GB, vol. 23, No. 4, Dec. 9, 2004 (Dec. 9, 2004), pp. 450-459, XP004629180, DOI:10.1016/J.VACCINE.2004. 06.022.
Oberyukhtina, I., Bogolitsyn, K., Popova, N., 2001. Physicochemical properties of solutions of sodium alginate extracted from brown algae *Laminaria digitata*. Russ. J. Appl., 74, 1645-1649.
Ohta, Masayoshi et al "Novel heparin/alginate gel combined with basic fibroblast growth factor promotes nerve regeneration in rat sciatic nerve", Journal of Biomedical Materials Research, Part A (2004), 71A(4).
Rodrigues A P et al: "Production and characterisation of alginate microparticles incorporating Aeromonas hydrophila designed for fish oral vaccination", Process Biochemistry, Elsevier, NL, vol. 41, No. 3, Mar. 1, 2006 (Mar. 1, 2006), pp. 638-643, XP027984270, ISSN: 1359-5113.
Sabyasachi Maiti and Biswanath SA: "Preparation and characterization of ibuprofen-loaded alginate microspheres using ethylenediamine as crosslinker", Oriental Pharmacy and Experimental Medicine, vol. 3, No. 8, Jan. 1, 2008 (Jan. 1, 2008), pp. 178-186, XP009191747.
Tønnesen H.H and Karlsen J "Alginate in Drug Delivery System", Drug Development and industrial Pharmacy, 28(6), (2002), p. 621-630.
Zhu J-Y et al: "Preparation and exosyndrome of sodium alginate hydrogel as a dermal tissue engineering scaffold", Zhongguo Zuzhi Gongcheng Yu Linchuang Kangfu = Journal of Clinical Rehabilitative Tissue Engineering Research, Zhongguo Kangfu Yixuehui, CN, vol. 12, No. 41, Oct. 7, 2008 (Oct. 7, 2008), pp. 8099-8102, XP009191703, ISSN: 1673-8225.
Joosten et al., "Oral vaccination of fish against Vibrio anguillarum using alginate microparticles" Fish & Shellfish Immunology, vol. 7, Issue 7, Oct. 1997, pp. 471-485 https://doi.org/10.1006/fsim.1997. 0100.

ORAL DELIVERY SYSTEM FOR BIOACTIVE AGENTS

CROSS-REFERENCE TO RELATED APPLICATIONS

This application is a Continuation of U.S. patent application Ser. No. 15/579,466, filed Dec. 4, 2017, which is a national phase application of PCT/N02016/050113, filed Jun. 2, 2016, which claims the benefit of Norwegian Patent Application No. 20150715, filed Jun. 3, 2015, and Great British Patent Application No. 1509608.4, filed Jun. 3, 2015, each of which is hereby incorporated by reference in its entirety.

FIELD OF THE INVENTION

The present invention relates to an oral delivery system, to ethylenediammonium alginate for use as an oral delivery system, and to a functional feed as defined in the introductory parts of the independent claims. Furthermore, the present invention relates to a method of producing ethylenediammonium alginate particles and to methods of producing a functional feed in pellet form comprising at least one bioactive agent.

BACKGROUND TO THE INVENTION

There is a high need for oral delivery systems of pharmaceutically active or bioactive drugs, compounds, and compositions for therapy and prophylactic purposes.

The optimal administration of these bioactive agents is crucial for their later uptake and efficacy in the organism. The way of how such bioactive agents are administered is therefor of great importance. Oral drug delivery is the method of swallowing a pharmaceutical compound with the intention of releasing it into the gastrointestinal tract of humans and animals.

During recent years, the use of functional ingredients in aquaculture industry has increased dramatically and a broad range of functional feeds are now widely available for use in fish farming. In connection with that, there is ongoing research dealing with the development of oral delivery systems for delivering of sensitive bioactive agents to fish. The most convenient and the least stressful method of administering drugs and other pharmaceutically active agents to farmed fish is via the feed.

During oral administration, one challenge is the potential deactivation or break down of active agents in the stomach before they can be absorbed in the gut. Many of the bioactive agents are thermo sensitive and prone to acidic and proteolytic degradation in the gastro intestinal tract. This is in particular the case for proteins. Another problem is the delivery to the right target organ for uptake as well as an efficient absorbance.

Insight into the digestive physiology of fish is thus very important for delivering bioactive agents such as therapeutic proteins via the oral route. Atlantic salmon (*Salmo salar*), which is an economically important species for the aquaculture industry, is a gastric fish with a rather short digestive system. The digestive tract of salmon being a carnivorous fish can be subdivided into a foregut (mouth, oesophagus and stomach), a midgut (pyloric ceca or proximal intestine and mid intestine) and a hindgut or a distal intestine terminating in the rectum. Digestion is a catabolic process of solubilising and degrading nutrients into smaller components that are more easily absorbed into a blood stream.

The major digestive components secreted in the stomach are pepsinogen and hydrochloric acid (HCl) and secretion of both of them are stimulated by feed intake. It was shown that an average gastric pH of 2.7 increases to 4.9 when the salmonid rainbow trout (Oncorhynchus mykiss) goes from starved to fed state (Bucking, C. and Wood, C. M. 2009. The effect of postprandial changes in pH along the gastrointestinal tract on the distribution of ions between the solid and fluid phases of the chyme in rainbow trout. Aquaculture Nutrition, Vol. 15, Issue 3, pp 282-296). The increased pH is maintained for eight hours post-feeding.

Most of the proteins are degraded by the action of HCl and pepsin in the stomach. After processing in the stomach, the mixture of dissolved nutrients and partially digested feed material passes into the pyloric caeca. The pyloric caeca constitute a compartment where other proteolytic enzymes like trypsin, chymotrypsin and aminopeptidase are completing the peptide hydrolysis. It is well known that most proteins are absorbed into the blood stream as free amino acids and short peptides in the pyloric region. When the acidic chyme reaches the proximal intestine, it becomes rapidly neutralised by bicarbonate ($HCO_3^-$) in bile and pancreatic juice. Bucking and Wood (2009) observed an average pH of 8.2 throughout the whole intestinal section in fasted fish. After feeding, the pH decreased to 7.5 in the proximal and mid intestine, while it remained almost unchanged in the distal section. However, the pH increased again in the period after feeding in the intestine, reaching its highest value after eight hours. At that point, the pH can be above 8.5 all along the intestinal tract with increasing trend towards the distal part.

Despite the harsh proteolytic environment in the foregut and midgut, some proteins make it through to the distal intestine where they can be absorbed. The distal intestine is considered to be the most important place of absorption of large peptides including antigens used in oral vaccines. It is therefore important that macromolecular agents such as proteins to be administered to fish, actually reach the distal part of the intestine for their efficient absorption. To protect macromolecular bioactive drugs against breakdown in the stomach, they are typically associated with oral delivery systems e.g., by encapsulation in a suitable polymer.

Another challenge for delivery of agents is that the passage time of feed material through the entire digestive system of carnivorous fish can be very short. The transit time depends on meal size, feed composition and structure, and it could be anything from 5 to 35 hours after feed intake.

The right choice of a suitable delivery agent is therefore of great importance. An important characteristic for the suitability of an oral delivery system is the proper dissolution of the delivery agent in order to release the bioactive composition at the right time and place in the intestinal system.

Cross-linked alginates are polymers which have typically been used in oral delivery systems. The cross-linking properties of alginate form the basis for various encapsulation techniques including both extrusion and emulsion processes. Alginates can be cross-linked using a variety of known cross-linking agents. The most commonly used cross-linking agent is $Ca^{2+}$.

A variety of products (nutrients, medicines, and vaccines) can be incorporated into alginate matrices to avoid damage from the low pH and proteolytic enzymes. Alginates are polysaccharides isolated from brown algae such as *Ascophyllum nodosum, Durvillaea* sp., *Ecklonia* sp., *Laminaria* sp., *Lessonia* sp., *Sargassum* sp. and *Macrocystis pyrifera* found in coastal waters around the globe. Marine alginates are composed of two forms of uronic acid: mannuronic (M) and guluronic (G). Two blocks of adjacent polymer chains can be cross-linked with multivalent cations (e.g., $Ca^{2+}$ or $Ba^{2+}$) through interactions with the carboxylic groups in the uronic acid, which leads to the formation of a gel network. The resulting cross-linked alginate has an excellent biocompatibility within host tissues and is able to biodegrade in a controlled manner. Bioactive agents for oral delivery are typically encapsulated or entrapped in alginate during the process of cross-linking, particularly by encapsulation into small alginate beads. Cross-linked alginate beads are typically stable at low pH and dissolve at higher pH. As a result, a faster release from alginate beads occurs in the intestine (alkaline conditions), after the beads have passed through the proteolytic and acidic environment of the stomach. These attributes make alginate an effective compound for use as an oral delivery system in humans and mammals.

Most studies carried out so far focused on the dissolution of alginate matrices under conditions which are relevant for the human digestive system such as pH 1.1-2.0 and pH 6.8-7.4 at a temperature of 37° C. As previously mentioned, it can be seen that pH>2.7 is most common in the stomach of salmonids. At the same time pH>7.5 is prevalent in the intestinal sections, although pH>8.5 is not an unusual condition either. Furthermore, gut passage rates and temperature conditions in the digestive processes are very different in poikilothermic animals compared to homiothermal organism such as mammals. As an example, the winter temperature could be below 4° C. while summer temperature could be at its most extreme above 18° C. in Norwegian seawaters, where Atlantic salmons are farmed.

Commonly known alginate matrices are not suitable or efficient for delivering bioactive agents to the lower gastrointestinal tract of animals with short intestine. The major shortcoming of commonly known oral delivery systems including alginate is incomplete or insufficient dissolution in the length-limited intestinal systems. This is especially the case in the gastric, carnivorous and omnivorous fish with preference to animal material which typically have a short intestinal tract such as salmonids, basses, breams, codfish, halibut, turbot, flounders, pangasius and grouper. Due to their short intestine, the retention time of feed material as well as the time window for release and uptake of active ingredients is rather limited.

Therefore, the objective technical problem of the present invention is to provide a vehicle for oral delivery of biologically active agents, particularly macromolecular drugs and therapeutic proteins to the intestine of animals.

Specifically, the present invention has the objective to provide a fast-dissolving and temperature-independent oral delivery system, in particular for species living in cold water.

More specifically, the present invention has the objective to provide an oral delivery system for use in fish, particularly in fish with a stomach and short intestinal tract.

Furthermore, the present invention has the objective to provide an oral delivery system for use in gastric, carnivorous and omnivorous fish, and in particular for cold water fish such as salmonids.

Another objective of the present invention aims to provide an oral delivery system that protects bioactive agents from acidic and proteolytic degradation in the stomach and then releases them in the intestinal region at an alkaline pH.

SUMMARY OF THE INVENTION

According to a first aspect, the present invention relates to an oral delivery system comprising ethylenediammonium alginate and at least one bioactive agent for use in a therapeutic and/or prophylactic treatment. This oral delivery system owing to its favourable dissolution properties is particularly suitable for use in animals, especially in animals with a short intestinal tract such as carnivorous and omnivores fish with preference to animal material. In particular, the oral delivery system is very well suitable for oral delivery of bioactive substances to ectothermic animals which can have a digestion at low temperatures.

Preferably, said bioactive agent is encapsulated or entrapped in ethylenediammonium alginate.

It is further preferred that the bioactive agent to be delivered is selected from the group consisting of proteins, peptides, vaccines, antibodies, antigens, hormones, enzymes, immune stimulants, drugs, probiotics, prebiotics, polynucleotides, nucleotides, and amino acids.

In a preferred embodiment, the oral delivery system is for use in an ectothermic animal with a gastrointestinal tract comprising an intestine and a stomach, preferably in a cold water species, more preferably in fish.

In another preferred embodiment, the present invention relates to an oral delivery system for use in a fish species selected from the group consisting of omnivorous and carnivorous species, preferably from a cold-water fish species.

In particular, the oral delivery system is suitable for use in fish, preferably in a gastric fish, more preferably for a fish with a short intestinal tract, most preferably in a species selected from a group consisting of salmonids, basses, breams, codfish, halibut, turbot, flounders, grouper, tuna, tilapia, and pangasius.

In a second aspect, the present invention relates to ethylenediammonium alginate for use as an oral delivery system in a therapeutic and/or prophylactic treatment. A preferred use is in fish, more preferably in an omnivorous or carnivorous species. Even more preferred is a use in a cold-water fish.

Preferably, the alginate matrix is in a form of particles, preferably as beads, and most preferably in form of spherical beads. Preferably the ethylenediammonium alginate beads have a mean particle size in the range of 1 µm to 10 mm, more preferably in the range of 300 µm to 2000 µm. In another preferred embodiment of the present invention, the mean particle size is no more than 300 µm, preferably is no more than 200 µm, more preferably is no more than 100 µm and most preferably is no more than 25 µm. This is an advantage when associating with feed pellet in a vacuum coater. Although the preferred mean size for pre-extrusional addition is less than 300 µm, the sizes between 300 µm and 2000 µm are feasible as well. Furthermore, the preferred mean size of alginate bead for standalone oral administration is greater than 100 µm and will depend on the size of both organism and target dose.

In a third aspect, the present invention relates to a functional feed comprising at least one bioactive agent encapsulated or entrapped in ethylenediammonium alginate. The incorporation of the alginate-encapsulated bioactive agent into feed pellets is an essential operation when it comes to animal feed, especially fish feed. Effective incorporation into a feed pellet reduces the loss of bioactive ingredients due to handling of feed and ensures a constant supply of prescribed doses.

Preferably, the alginate comprising the bioactive agent in the functional feed is in form of beads.

Preferably, the ethylenediammonium alginate is shaped as particles, preferably as beads and most preferably in form of spherical beads. In a preferred embodiment according to the present invention the mean particle size of the alginate beads is no more than 2000 μm, preferably no more than 1000 μm, more preferably no more than 300 μm, and most preferably no more than 25 μm.

In yet another aspect the present invention relates to a functional feed comprising at least one bioactive agent encapsulated in ethylenediammonium alginate for use in therapeutic and/or prophylactic treatment. A preferred use of the functional feed is in fish.

In yet another aspect, the present invention relates to a method of producing ethylenediammonium alginate particles comprising at least one bioactive agent by a process of cross-linking alginate with ethylenediammonium whereby the desired alginate shape is formed by means of (i) an extrusion method prior to curing in an ethylenediammonium solution or (ii) an emulsion method. In said process, the desired alginate shape and size are either formed by means of the extrusion method prior to curing in an ethylenediammonium solution or by the emulsion method in combination with said ethylenediammonium.

The extrusion method (i) can be selected from a group consisting of aerodynamically assisted jetting, electromagnetic laminar jet breakup, inkjet printing, 3D printing, electro spraying, and coaxial air flow induced dripping and wherein the emulsion method (ii) can be a method selected from the group consisting of coacervation, internal gelation, and external gelation.

The method can comprise the following steps:
(i) preparing an encapsulation formulation by dissolving alginate in a solution comprising at least one bioactive agent to be delivered,
(ii) creating a jet of alginate droplets with aid of air pressure by extruding the solution of (i) through a nozzle of relevant size situated in a pressurised chamber fitted with an exit orifice of size in conformity with a said nozzle,
(iii) focusing the jet of droplets of (ii) onto the cross-linking solution comprising ethylenediamine dihydrochloride, followed by
(iv) filtering off the obtained alginate beads.

Furthermore, the present invention relates to a method of producing a functional feed comprising at least one bioactive agent wherein the method comprises the following steps:
(i) preparing an oil suspension comprising ethylenediammonium alginate beads wherein an bioactive agent has been entrapped or encapsulated,
(ii) mixing the suspension of (i) with feed pellets in a vacuum coater,
(iii) evacuating air from a coater creating an environment with reduced pressure, and
(iv) gradually regaining atmospheric pressure by letting the air back into the coater which pushes the suspension of (i) into the empty pores of feed pellets.

Besides a post-extrusional inclusion of the said encapsulated bioactive agent(s) in the feed, a pre-extrusional inclusion of the said encapsulated bioactive agent(s) is possible.

In yet another aspect the present invention relates to a method of producing functional feed containing at least one bioactive agent wherein the method comprises the following steps:
(i) preparing a dry mix by mixing ethylenediammonium alginate beads containing at least one bioactive agent with a feed flour comprising other non-oil feed ingredients,
(ii) preparing an extrudate by extruding the dry mix of (i) by using an extruder or by using a pellet press,
(iii) producing base pellets by drying the extrudate of (ii) in a dryer, and
(iv) producing final feed by oil coating the base pellets of (iii) in a vacuum infusion coating process.

Preferred embodiments are also defined in the dependent claims.

DESCRIPTION OF THE INVENTION

Figure 2:
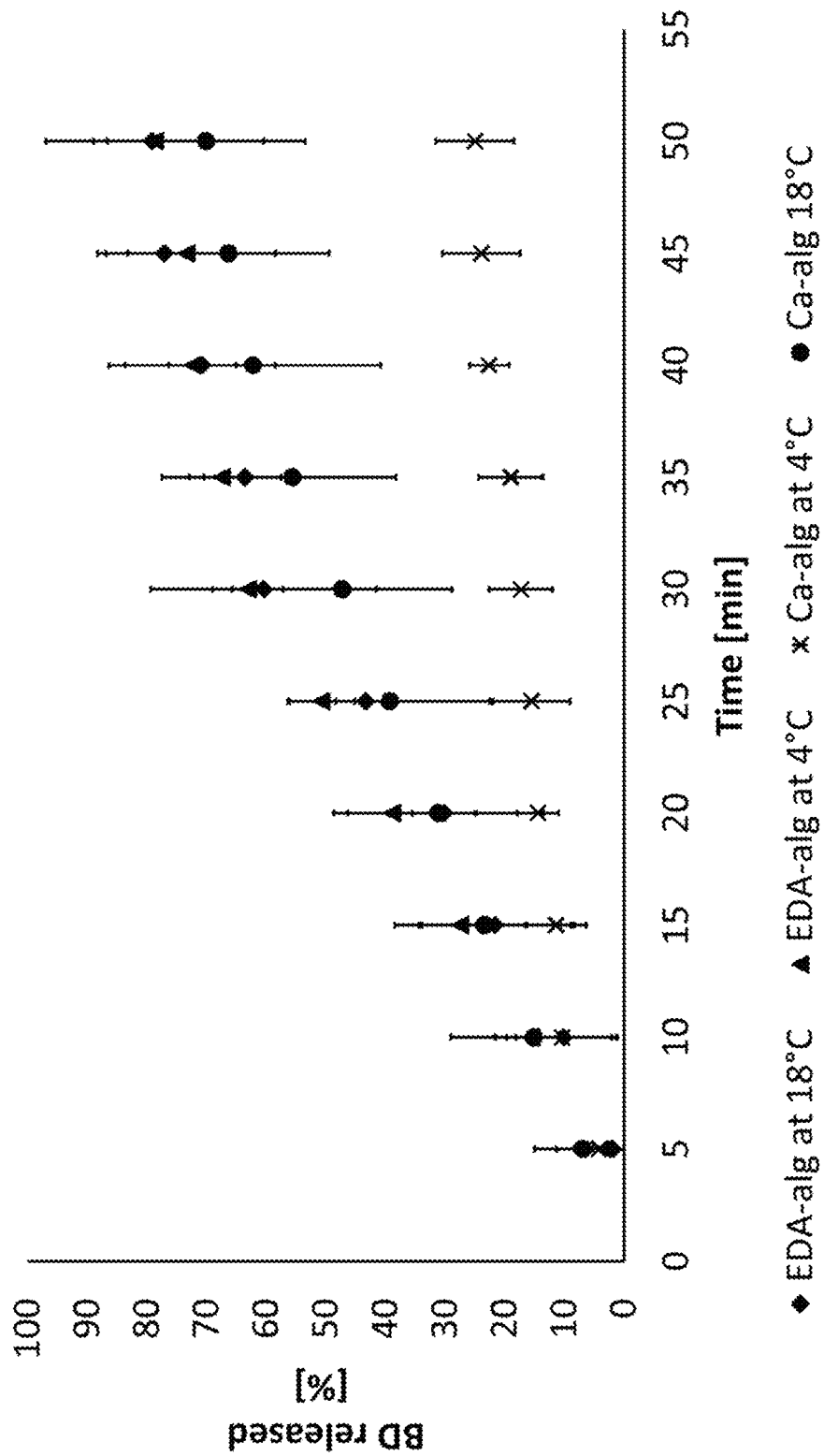
Figure 3:
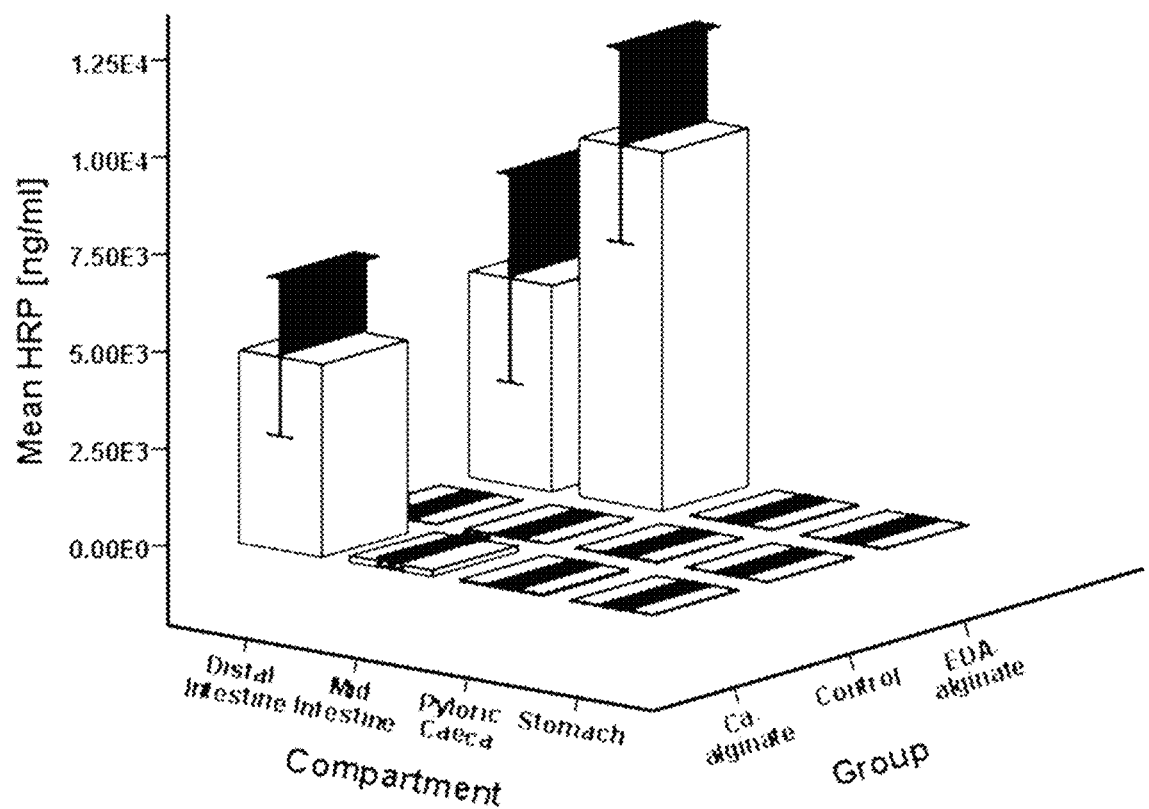

Embodiments of the invention will now be described, by the way of examples with reference to the following diagrams, wherein FIG. 1 shows stereomicroscope (SMZ) images (Leica MZ10 F) of a) Ca-alginate beads loaded with blue dextran (BD-Ca-alg; $d_{mean}$=3.0 mm), b) EDA-alginate beads loaded with blue dextran (BD-EDA-alg; $d_{mean}$=3.7 mm);

FIG. 2 shows dissolution profiles as curves of the mean percentage of cumulative blue dextran (BD) release from alginate beads over time. Dissolution tests performed in potassium hydrogen phthalate/HCl buffer (pH 3.0) for 15 min followed by phosphate buffer (pH 8.0) for the next 50 min. Release was below LoQ ($3.9 \times 10^{-3}$ mg ml$^{-1}$) in the acidic medium so the figure depicts only release in the alkaline dissolution medium. The error bars represent standard deviation (SD) based on five samples at each point. BD-EDA-alg denotes ethylenediammonium alginate beads loaded with BD; BD-Ca-alg means calcium alginate beads loaded with BD;

FIG. 3 shows the HRP concentration in four gastrointestinal compartments (stomach, pyloric caeca, mid and distal intestine) of three groups of A. salmon (Ca-alginate, EDA-alginate and Control). The error bars represent 95% confidence intervals. The Ca-alginate group received calcium alginate encapsulated HRP (HRP-Ca-alg). EDA-alginate group received ethylenediammonium alginate encapsulated HRP (HRP-EDA-alg). The Control group did not receive any HRP.

The present invention provides a novel oral delivery system for delivery of bioactive agents to the intestine. This oral delivery system is particularly suitable for use in organisms with a short intestinal tract such as carnivorous fish. In particular, the oral delivery system is suitable for oral delivery of bioactive substances in ectothermic animals which can have a digestion at low temperatures.

In the present invention sodium alginate is cross-linked with ethylenediamine dihydrochloride to form ethylenediammonium alginate. The advantage of this method is that no other chemicals are involved. Furthermore, the described method to cross-link alginate with ethylenediammonium hydrochloride is faster, easier, less expensive, and does not involve dangerous chemicals compared to other known methods.

In accordance with the present invention, ethylenediammonium alginate is used as an oral delivery system for bioactive agents, in particular in fish. The agents are encapsulated or entrapped in the matrix of ethylenediammonium alginate during the process of cross-linking alginate with ethylenediammonium dications. Preferably, small alginate microbeads are produced during this cross-linking process consisting of two major steps: 1) generating of alginate droplets by devices such as spray or jetting heads fitted with nozzles as those found in aerodynamically assisted jetting or by other methods known to the skilled person for generating droplets of liquids (e.g. aerodynamically assisted jetting, electromagnetic laminar jet breakup, inkjet printing, 3D printing, electro spraying, coaxial air flow induced dripping etc.); 2) collecting alginate droplets in cross-linking solution containing ethylenediammonium. Alternatively, an emulsion method (e.g., coacervation, internal and external gelation etc.) can be used in combination with ethylenediammonium.

The ethylenediammonium alginate matrix can typically have the form of any geometric particle shape for particles e.g., fibre, sphere, toroid, ellipsoid and also including fibres and flakes. Preferably, the particles are regular shaped, although said alginate matrix can also be in form of an irregularly shaped particle. In a preferred embodiment said matrix is in form of beads, more preferred in form of spherical beads.

The resulting alginate beads comprising bioactive agent(s) can be enterally administered either in feed or ex feed (independently, without regard to feed) to target organisms. The preferred mean particle size of the alginate beads is in the range of 1 μm to 10 mm. For associating with feed pellets in a vacuum coater the mean size of alginate beads can typically be in the range of 300 μm and 2000 μm. However, the preferred mean size for pre-extrusional addition is less than 300 μm. Preferred particles sizes are less than 300 μm, more preferable less than 100 μm and most preferable less than 25 μm. The preferred mean size of alginate beads for stand-alone administration (without being in cooperated in a feed) is greater than 100 μm. For this use the preferred size of the beads will typically depend on both, the size of the animal and target dose and may be adjusted correspondingly. However, the preferred route of administration to fish is the oral route with alginate beads in feed.

The small alginate beads comprising bioactive agent(s) are preferably incorporated into feed pellets by a suitable method such as vacuum infusion coating, before they are orally administered to target organisms, such as a fish. Alternatively, the beads can be mixed with other feed ingredients before pelletizing. These ingredients can for example be conventional feed components known to a skilled person. Preferably, the alginate beads comprising one or several bioactive ingredient(s) are mixed with initial flour (dry mix consisting of all feed ingredients except from oil) prior to extrusion or any other means of making feed pellets.

A detailed description of a preferred method in agreement with the present invention for cross-linking of alginate with ethylenediamine dihydrochloride as well as a preferred method for production of small ethylenediammonium alginate beads loaded with one or more bioactive agents is provided in the experimental section below. Furthermore, a preferred method according to the present invention for incorporating the alginate beads into feed pellets is provided in said experimental section.

Experimental Section:

The efficacy of ethylenediammonium alginate (EDA-alginate) was tested and proved in two different experimental settings in vitro and in vivo. Results obtained were compared to a common oral delivery system based on alginate cross-linked with $Ca^{2+}$ (Ca-alginate).

As described above, the digestive conditions in fish, being ectothermic and especially in carnivorous fish having a short intestine, differs from those of many other organisms, especially from mammals and humans. Therefore, in the present invention, the oral delivery system according to the present invention was tested both, in a known standard dissolution test as well as in a test, which has been adapted to the digestive conditions that are representative for ectothermic salmonid fish. Firstly, release of blue dextran from Ca-alginate and EDA-alginate was assessed in vitro in a standard dissolution test (pH 1.2 and pH 6.8 at 37° C.). Secondly, release from the same alginates was tested in alkaline dissolution media of pH 8.0 and pH 8.6 at 18° C. Based on the results from the previous tests, a new dissolution test strategy (pH 3.0 followed by pH 8.6 at 4° C. or at 18° C.) was developed. Finally, release of horseradish peroxidase (HRP) from both Ca-alginate and EDA-alginate was assessed in vivo in a feeding trial to prove the suitability of ethylenediammonium alginate as an oral delivery system for macromolecules in fish.

4.1 Materials Used in the Experiments

Sodium alginate (Protanal LF 20/40) was obtained from FMC BioPolymer AS (Norway). Horseradish Peroxidase (HRP, P/N 31491, Thermo Fisher Scientific) was acquired from Perbio Science UK Ltd. Deionised water (DI water, analytical reagent) was purchased from Fishe Chemical Ltd. (UK). The following reagents were purchased from VWR Ltd (UK): calcium chloride dihydrate (AnalaR NORMAPUR®, ACS analytical reagent), sodium bicarbonate (AnalaR NORMAPUR®, ACS analytical reagent), sodium hydroxide (≥98%, flake, Alfa Aesar), potassium hydrogen phthalate (≥99%, Alfa Aesar) and hydrochloric acid (37%, AnalaR NORMAPUR®, analytical reagent). The following reagents were purchased from Sigma-Aldrich Ltd. (UK): ethylenediamine dihydrochloride (98%, Aldrich), glycine (≥99%, ReagentPlus®), disodium phosphate dihydrate (≥99%, analytical reagent), monosodium phosphate dihydrate (≥98%, analytical reagent), blue dextran, BD (M.W=2,000,000; [reactive blue 2]=0.10 to 0.12 mmol $g^{-1}$ dextran) and 3,3',5,5'-tetramethylbenzidine (TMB) liquid substrate system (ready to use). EWOS Opal 200 base pellet (BP, 5.8% fat) was produced at Technology Centre of EWOS Innovation AS in Dirdal (Norway). Fish oil (EWOS ID: 20180) was acquired from Egersund Sildolj efabrikk AS (Egersund, Norway).

Stock Solutions:

Blue dextran encapsulation formulation (BD-EncForm) was prepared by dissolving sodium alginate (2.0% w/v) in a BD solution (50.0 mg $ml^{-1}$) at ambient temperature.

Buffer pH 1.2: Sodium chloride/hydrochloric acid (NaCl/HCl, pH 1.2) buffer was prepared by mixing NaCl solution (250 ml, 23.38 g $l^{-1}$, 0.4M NaCl) with 0.4M HCl solution (425 ml). Before making up the volume to 1000 ml with DI water, the pH of the buffer solution was adjusted to 1.2.

Buffer pH 3.0: Potassium hydrogen phthalate solution (500 ml, 81.69 g $l^1$, 0.4M KPH) was combined with HCl solution (223 ml, 0.4M HCl) to produce stock solution of KPH/HCl buffer (pH 3.0). The buffer solution was replenished with DI water to a total volume of 1000 ml.

Buffer pH 6.8: Monosodium phosphate dihydrate solution (255 ml, 62.40 g 0.4M $NaH_2PO_4 \cdot 2H_2O$) was mixed with disodium phosphate dihydrate solution (245 ml, 71.20 g $l^{-1}$, 0.4M $Na_2HPO_4 \cdot 2H_2O$) to form phosphate buffer (pH 6.8). The resulting buffer was adjusted to pH 6.8 before levelling the volume to 1000 ml with DI water.

Buffer pH 8.0: Phosphate buffer (pH 8.0) was made by combining monosodium phosphate dihydrate solution (26.5 ml, 62.40 g $l^{-1}$, 0.4M $NaH_2PO_4 \cdot H_2O$) with disodium phosphate dihydrate solution (473.5 ml, 71.20 g $l^{-1}$, 0.4M $Na_2HPO_4 \cdot 2H_2O$). The resulting buffer solution was adjusted to pH 8.0 and then diluted with DI water to a final volume of 1000 ml.

Buffer pH 8.6: Glycine solution (250 ml, 30.03 g $l^{-1}$, 0.4M Gly) was mixed with sodium hydroxide solution (20 ml, 16 g $l^{-1}$, 0.4M NaOH) to produce Gly/NaOH buffer. After adjusting the pH to 8.6, the generated buffer solution was diluted to a volume of 1000 ml with DI water.

Sodium bicarbonate (150 g $l^{-1}$, $NaHCO_3$) was dissolved in DI water to produce a saturated $NaHCO_3$ solution. Any undissolved $NaHCO_3$ crystals were filtered off prior to use.

Horseradish Peroxidase (HRP) encapsulation formulation (HRP-EncForm) was prepared by dissolving sodium alginate (2.0% w/w) in an HRP solution (400 μg ml$^{-1}$ of DI water) at 4° C.

HRP stock solution (5 mg ml$^{-1}$) was prepared by dissolving HRP powder (10.0 mg) in DI water (2.0 ml). Aliquots of this HRP solution (20.0 μl) were stored at −20° C. prior to constructing the standard curves in the enzyme assay.

The cross-linking solutions (CaCl$_2$) sol. and EDA·2·HCl sol.) were prepared by separately dissolving calcium chloride dihydrate (36.8 g l$^{-1}$, 0.25M CaCl$_2$·2H$_2$O) and ethylenediamine dihydrochloride (33.3 g l$^{-1}$, 0.25M EDA·2HCl) in DI water.

4.2 In Vitro Test of Dissolution of Alginate Microbeads

Blue dextran (BD) was selected as a model compound for the simulated release of active pharmaceutical ingredients (API) from alginate matrices.

Preparation of Alginate Beads Loaded with Blue Dextran

BD-EncForm ([BD]=50.0 mg ml$^{-1}$) was extruded from a 60 ml plastic syringe (BD Plastipak™) through a needle (i.d.=2.0 mm) into the cross-linking solutions. Flow rate (50.00 ml h$^{-1}$) was maintained constant by a syringe pump (Harvard PHD4400, Harvard Apparatus Ltd, Edenbridge, UK) working in the volume mode (target volume=1.50 ml). This set up was used to extrude 80 batches of BD-EncForm a 1.50 ml each. The cross-linking solutions, CaCl$_2$) sol. (40×10.0 ml) and EDA·2HCl sol. (40×10.0 ml) were used to yield BD-Ca-alg (40 batches) and BD-EDA-alg beads (40 batches) respectively. Common to each batch was that alginate beads were separated from the cross-linking solution 10 min after the last bead was generated. Thereafter, the recovered alginate beads loaded with BD were washed with DI water (3×5 ml). BD-Ca-alg (10 batches) and BD-EDA-alg beads (10 batches) were used to determine encapsulation efficiency while the remaining batches were utilised in dissolution tests. The particle size distribution and shape were determined by a stereo microscope (Leica MZ10 F, Leica Microsystems, Wetzlar, Germany).

Encapsulation Efficiency of Blue Dextran

BD-Ca-alg (10 batches) and BD-EDA-alg (10 batches) beads were added to saturated NaHCO$_3$ solution (20×9.0 ml, pH=8.0). As a result, all beads were completely dissolved after two hours under stirring. To equalise all sample volumes, the level of the resulting solutions was adjusted to 10 ml with DI water. These newly created solutions (n=20) were filtered through syringe filters (0.45 VWR) prior to application onto a 96-well polystyrene plate (Nunc™, Sigma-Aldrich) for an endpoint assay. Absorbance of BD was measured using a VERSAmax microplate reader (Molecular Devices LLC, Sunnyvale, Calif., USA) at 610 nm and 24° C. BD concentration of the samples was determined by using standard curve in the range of 1.0 to 3.9×10$^{-3}$ mg ml$^{-1}$. Standard curves were generated by plotting BD concentrations of nine two-fold serial dilutions of BD solution (1.0 mg ml$^{-1}$) versus absorbance. The BD solution (1.0 mg ml$^{-1}$) was derived from BD-EncForm ([BD]=50.0 mg ml$^{-1}$) using saturated NaHCO$_3$ solution as a diluent.

A. Standard Dissolution Test

Dissolution tester (Caleva 8ST, Caleva International Ltd, UK) equipped with dissolution vessels (V=1000 ml) and rotating stainless steel baskets (40 mesh) was used to assess BD release from the two different types of alginate beads. This setup was in compliance with the standard requirements for Apparatus 1 set by United States Pharmacopoeia (USP) and described in the General Chapter <711>.

Dissolution medium (300 ml; NaCl/HCl buffer, pH 1.2 or phosphate buffer, pH 6.8) was added into each of the vessels and then allowed to temperate overnight at 37° C. The dissolution experiment started within 2 h after producing alginate beads according to the method described above. The alginate beads (BD-Ca-alg or BD-EDA-alg) were placed into rotating baskets (100 rpm) and then submerged into dissolution vessels. The following experiments were carried out in quintuplicate at 37° C.: Test 1) BD-Ca-alg at pH 1.2, Test 2) BD-EDA-alg at pH 1.2, Test 3) BD-Ca-alg at pH 6.8 and Test 4) BD-EDA-alg at pH 6.8.

Samples (1.0 ml sample$^{-1}$) were taken from the vessel at five minutes intervals through an extent of 50 minutes. An equivalent volume of dissolution medium (1.0 ml, 37° C.) was then added to keep the liquid level in the vessels constant. All samples were filtered through a syringe filter (0.45 VWR) before placing them onto a 96-well polystyrene plate (Nunc™ Sigma-Aldrich) for an endpoint assay. Reading of the plate was performed by a VERSAmax microplate reader (Molecular Devices LLC, Sunnyvale, Calif., USA) at 610 nm and 24° C. Amount of BD released was determined by applying standard curve approach. Standard curves were generated by plotting BD concentrations of nine two-fold serial dilutions of BD solution (1.0 mg ml$^{-1}$) versus absorbance in the range of 1.0 to 3.9×10$^{-3}$ mg ml$^{-1}$. The BD solution (1.0 mg ml$^{-1}$) was derived from BD-EncForm ([BD]=50.0 mg ml$^{-1}$) using the experimental buffer as a diluent.

B. Assessment of Alkaline Dissolution Media

In order to select an alkaline dissolution medium, which is representative for the salmon intestine in terms of temperature and pH, four dissolution tests were carried out as described in the previous section. The following experiments were performed with five replications each in dissolution media (phosphate buffer, pH 8.0 and Gly/NaOH buffer, pH 8.6) at 18° C.: Test 5) BD-Ca-alg at pH 8.0, Test 6) BD-EDA-alg at pH 8.0, Test 7) BD-Ca-alg at pH 8.6, and Test 8) BD-EDA-alg at pH 8.6. The concentration of BD in the samples was determined in the same way as previously described in the standard dissolution test.

C. A New Dissolution Test Strategy Adapted to Fish

The applied conditions in this test were in accordance with the conditions that alginate beads could typically be exposed to during their passage through gastrointestinal tract of A. salmon. Accordingly, alginate beads were first submerged into acidic dissolution medium (KPH/HCl buffer, pH 3.0) for 15 min and then the acidic buffer solution was replaced with an alkaline dissolution medium (phosphate buffer, pH 8.0). In this test, the same UPS Apparatus 1 as previously described was used. In order to replicate the natural conditions in which A. salmon lives as fully as possible, two different temperatures (4° C. and 18° C.) were applied in the test. The chosen temperatures typically correspond to the water temperatures during summer and winter at the Norwegian coast. For this reason, the following four dissolution tests were carried out in quintuplicate: Test 9) BD-Ca-alg at pH 3.0-8.0 and 4° C., Test 10) BD-EDA-alg at pH 3.0-8.0 and 4° C., Test 11) BD-Ca-alg at pH 3.0-8.0 and 18° C., Test 12) BD-EDA-alg at pH 3.0-8.0 and 18° C. The first sample was taken after 15 min in the KPH/HCl buffer (pH 3.0). Further sampling, which started 5 min after replacing the dissolution medium, was conducted as previously described in the standard method. Similarly, the endpoint assay was carried out according to the method described in in the preceding sections. Encapsulation efficiency of BD was taken in consideration when calculating percentage release from alginate beads.

Statistical Analysis

Dissolution profiles of BD shown as curves of the mean percentage of cumulative BD release with error bars (95% confidence intervals) over time were generated using Data analysis and Scatter plot functions in Microsoft Excel 2010.

Results

The average encapsulation efficiency of BD in BD-Ca-alg and BD-EDA-alg was 90% (SD=4%) and 70% (SD=4%), respectively. Mean size of the Ca-alginate beads was 3.0 mm while the mean size of the EDA-alginate beads was 3.7 mm. The shape of the beads was spherical for both types of beads (FIG. 1).

Release of BD from both Ca-alginate and EDA-alginate beads was below the quantification limit (LoQ=3.9×10$^{-3}$ mg ml$^{-1}$) of the assay in the standard dissolution tests (Test 1 and 2 performed in pH 1.2 at 37° C.; Test 3 and 4 performed in pH 6.8 at 37° C.).

Similarly, the release of BD from both alginate beads was below LoQ in the tests carried out in the alkaline dissolution media (Test 5 and Test 6 performed in pH 8.0 at 18° C.; Test 7 and Test 8 performed in pH 8.6 at 18° C.). From the present in vitro study it could be seen that both Ca-alginate and EDA-alginate matrix are poorly soluble in buffers with pH 1.2 at 37° C., pH 6.8 at 37° C., pH 8.0 at 18° C. and pH 8.6 at 18° C. within a time frame of 50 minutes.

In the dissolution tests (Test 9-12) adapted to the conditions in which salmonid fish digest alginate, significant release of BD was observed in all four experiments. The release, which was below LoQ at pH 3.0, was fairly rapid after raising the pH from pH 3.0 to pH 8.0. From Test 12 at 18° C. (FIG. 2), it can be seen that 50% of BD was released from BD-EDA-alg after 23 min, while 85% of BD was released after 40 min. As seen in the Test 10 with the same BD-EDA-alg beads carried out at 4° C., 50% and 85% release was recorded after 19 and 39 min respectively. The dissolution rate of BD-Ca-alg (Test 11) was somewhat lower at 18° C. than the release rate from BD-EDA-alg at both 4° C. and 18° C. As a result, 50% of BD was free in solution after 26 min. In addition, 85% of BD was released within 48 min. However, with only 30% of BD dissolved after 49 min, the dissolution rate of BD-Ca-alg at 4° C. (Test 9) was much lower compared to the other three tests. The preceding estimations of dissolution rates were calculated using the second-order approximations shown in the Table 1.

TABLE 1

Dissolution curves related to the release of blue dextran release (BD) from calcium (BD-Ca-alg) and ethylenediammonium alginate (BD-EDA-alg) at 4° C. and 18° C. First- and second-order approximations of dissolution curves are shown with corresponding coefficients of determination ($R^2$). Data fits very well both linear and non-liner function in the time interval 0 to 50 minutes after changing dissolution medium.

| Product | Order | Dissolution curves | $R^2$ |
|---|---|---|---|
| BD-EDA-alg | $1^{st}$ | $y = 2.2101x - 3.9877$ | 0.97 |
| at 18° C. | $2^{nd}$ | $y = -0.0112x^2 + 2.7696x - 8.1836$ | 0.98 |
| BD-EDA-alg | $1^{st}$ | $y = 2.1061x + 2.251$ | 0.96 |
| at 4° C. | $2^{nd}$ | $y = -0.0264x^2 + 3.4249x - 7.6404$ | 0.99 |
| BD-Ca-alg | $1^{st}$ | $y = 1.8109x + 1.7095$ | 0.99 |
| at 18° C. | $2^{nd}$ | $y = -0.01x^2 + 2.3088x - 2.0247$ | 1.00 |
| BD-Ca-alg | $1^{st}$ | $y = 0.5760x + 4.0063$ | 0.95 |
| at 4° C. | $2^{nd}$ | $y = -0.0067x^2 + 0.91121x + 1.4852$ | 0.98 |

Drugs, which are encapsulated in alginate matrices, are principally released by two mechanisms: 1) diffusion of the drug through the pores of the polymer network and 2) degradation of the polymer network. Unlike low molecular weight drugs, blue dextran (M.W.=2,000,000) is so large that it cannot diffuse through the pores of an alginate matrix without their further expansion (Kim, C. and Lee, E., 1992. The controlled release of blue dextran from alginate beads. Int. J. Pharm. 79, 11-19). Therefore, most of the BD release from alginate matrices presumably happens due to degradation of the polymer network. In earlier studies a very low release rate of fluorescein isothiocyanate dextran (M.W.=145,000) was observed at pH 7.4 during the first hour.

Very little degradation of EDA-alginate is expected to occur at pH 3.5-7.0 since most of the ethylenediamine (uncharged form) will exist as ethylenediammonium (positively charged) at a pH<7.0 and most of the alginate (alginic acid) will be deprotonated (negatively charged) at pH>3.5.

According to the experimental results presented in the present invention, an effective way to weaken the cross-linked structure of an alginate matrix is to use an acidic dissolution medium (pH<3.5) before applying an alkaline medium (pH>7.0). Without being bound to theory, the following mechanism may apply: At a pH below 3.5 (alginic acid, pKa=1.5-3.5), hydrogen ions ($H^+$) apparently replace ethylenediammonium in alginate networks yielding an unlinked structure of alginic acid. Although alginic acid is poorly water soluble, it is easily convertible to an aqueous soluble form (e.g., sodium alginate) at higher pH. At the same time, an increasing alkaline pH (pH>7.0) is reducing the crosslinking strength of ethylenediammonium through deprotonation of its amine groups and conversion to ethylenediamine, the uncharged form. As a consequence, a foregoing treatment with acidic medium (pH<3.5) may give much faster release rate than the direct treatment with an alkaline medium (pH>7.0). Therefore, the standard conditions commonly applied in dissolution tests (pH=1.2 and 6.8 at 37° C.) very often result in very slow dissolution rates.

By subsequent application of media with pH=3.0 followed by pH=8.0, the high release rates shown in the FIG. 2 were achieved. As mentioned above, putting alginate beads in an acidic buffer (pH=3.0) for a short period of time seems to convert some EDA-alginate to alginic acid. Consequently, alginic acid and any remaining EDA-alginate will be readily dissolved when acidic buffer is replaced with an alkaline buffer (pH=8.0) while EDA will become less charged. In the same manner, disintegration rate of Ca-alginate matrix is accelerating with increasing pH of the dissolution medium. At the same time, attraction of charged sodium ($Na^+$) towards carboxylic groups of alginate is increasing when the pH is greater than 8 (Oberyukhtina, I., Bogolitsyn, K., Popova, N., 2001. Physicochemical properties of solutions of sodium alginate extracted from brown algae *Laminaria digitata*. Russ. J. Appl., 74, 1645-1649). On the other hand, calcium phosphate may already start precipitating from a system containing $Ca^{2+}$ and phosphate buffer at pH>6.7 (Feenstra, T. P., De Bruyn, P. L., 1979. Formation of calcium phosphates in moderately supersaturated solutions. J. Phys. Chem. 83, 475-479). By way of the present invention and the new developed dissolution test strategy, it could be shown that EDA-alginate has a high efficiency and potential as oral delivery system under conditions typically found in fish, where the gastric pH is 2.7-4.9 and the intestinal pH is 7.5-8.5.

It is generally known that the dissolution of cross-linked alginates is pH-dependent and temperature dependent. From the FIG. 2, it can be concluded that dissolution of EDA-alginate is pH-dependent, but surprisingly not affected by temperature in the range of 4-18° C. In contrast, the release rate of BD from the Ca-alginate matrix was significantly lower than the release rate from both EDA-alginate at 4° C. and Ca-alginate at 18° C. This is in agreement with the results from the in vivo trial which was carried out at 5° C. (see below). Thus, by way of the present invention, it could be proven that ethylenediammonium alginate is particularly suitable as an oral delivery system in poikilothermic organisms such as fish.

4.3 In Vivo Test of Dissolution of Alginate Microbeads

Performance of ethylenediammonium alginate as an oral delivery system according to the present invention was further tested in an in vivo experiment with Atlantic salmon (*Salmo salar*).

Preparation of Alginate Microbeads Loaded with HRP:

Calcium alginate (HRP-Ca-alg) and ethylenediammonium alginate (HRP-EDA-alg) microbeads loaded with HRP were produced in an encapsulation process referred as aerodynamically assisted jetting. In the process of aerodynamically assisted jetting, jet of alginate droplets was generated by extruding HRP-EncForm (2×240.0 g) through a jetting head by means of air pressure. The jetting head was fitted with a nozzle (Ø=500 µm) and an exit orifice (Ø=500 µm) of the same size. The created jet was directed towards the surface of a cross-linking solution from a distance of 100 mm. The cross-linking solutions, $CaCl_2$) sol. (500 ml, 4° C.) and EDA·2HCl sol. (500 ml, 4° C.) were used to yield HRP-Ca-alg (240.0 g) and HRP-EDA-alg (240.0 g) microbeads, respectively. The flow rate (100 ml h$^{-1}$) of the alginate solution was controlled by a high precision syringe pump (PHD 4400, Harvard Apparatus Ltd, Edenbridge, UK). The air pressure in the process was maintained at 3.00 bar by a precision regulator (IR1000, SMC Corporation, Tokyo, Japan). The resulting microbeads were filtered off by suction filtration and washed with DI water (3×20 ml) before storing at −20° C. The obtained mass of HRP-Ca-alg and HRP-EDA-alg microbeads was 81.54 g and 78.29 g, respectively. Laser diffraction system (HELOS BR CUVETTE, CUV-50ML/US, optical module R5, Sympatec GmbH, Clausthal-Zellerfeld, Germany) was used to measure the size of generated alginate beads at wavelength λ=632.8 nm. The median diameter of the microbeads was 25-26 µm.

If the obtained beads shall be incorporated into a feed pellet via the surface, than the diameter of the microbeads must correspond to the pore size of the pellet. This is achieved by the above-described method.

Preparation of the Experimental Feeds

Two experimental feeds (5.0 kg a batch) comprising HRP were produced by applying HRP-alg microbeads ($d_{median}$=25-26 µm) suspended in fish oil (1210.0 g) to EWOS Opal 200 base pellet (BP) in a vacuum infusion coating process (Table 2).

TABLE 2

Composition of the experimental feeds
HRP-Ca-feed, HRP-EDA-feed and Ctrl-feed

| Feed name | Oil mixture | | | BP[iii] [g] | Total [g] |
|---|---|---|---|---|---|
| | Fish oil [g] | HRP-Ca-alg[i] [g] | HRP-EDA-alg[ii] [g] | | |
| Ctrl-feed | 1210.00 | 0.00 | 0.00 | 3790.00 | 5000.00 |
| HRP-Ca-feed | 1210.00 | 81.54 | 0.00 | 3708.46 | 5000.00 |
| HRP-EDA-feed | 1210.00 | 0.00 | 78.29 | 3711.71 | 5000.00 |

[i]HRP-Ca-alg - product generated by encapsulating HRP solution into Ca-alginate matrix
[ii]HRP-EDA-alg - product made by encapsulating HRP solution into EDA-alginate matrix
[iii]BP - base pellet is a semi-finished fish feed product, dry extrudate lacking oil mix HRP-Ca-feed was prepared by coating BP (3708.46 g) with oil suspension containing HRP-Ca-alg (81.54 g) while HRP-EDA-feed was made ready by applying oil suspension containing HRP-EDA-alg (78.29 g) to BP (3711.71 g) in a vacuum coater. Control feed (Ctrl-feed) without HRP was produced by coating BP (3790.00 g) with fish oil (1210.00 g) only.

Fish Trial

Atlantic salmon *Salmo salar* (Total number: n=495, $m_{avg}$=394 g) were distributed randomly among nine circular seawater tanks (d=1 m, V=0.5 m$^3$, $t_{water}$=5° C.) at EWOS Innovation AS (Dirdal, Norway) nine weeks prior to the start of the trial. The tanks were randomly divided into three groups (Ca-alginate, EDA-alginate and Control), with three tanks being assigned to each group. After a nine weeks long acclimatisation stage, the Ca-alginate and EDA-alginate group of fish were treated with HRP-Ca-feed and HRP-EDA-feed, respectively. The Control group was fed Ctrl-feed. The treatment lasted for two weeks after which followed a sampling. The health status of the fish was very good during the 11 weeks long span of the trial.

Sampling

Prior to sampling, fish (n=15 fish per tank) were anaesthetised with Finquel® (100 mg l$^{-1}$). Weight of individual fish was recorded for each sampled fish. The following samples were collected 1) Stomach, 2) Pyloric Caeca, 3) Mid intestine, and 4) Distal intestine. Each of the sampled gastrointestinal compartments was opened by longitudinal incision and placed into a container with DI water (10.0 ml, t=4° C.). After vigorous shaking, the solid content was separated from the liquid phase by gravity filtration. The resulting filtrate (2 ml) from each container was transferred to an Eppendorf tube and stored at −20° C. until assayed.

Sample Analysis

The samples were thawed and spun down at 4000 rpm for four minutes prior to use. Stomach and pyloric caeca samples were applied undiluted while mid and distal intestine samples were diluted 1:200 with DI water (4° C.) before assaying. For diluted mid and distal intestine samples (1:200) below quantification limit (0.391 ng ml$^{-1}$), lower dilutions like 1:10 and 1:100 or no dilution were used to increase sensitivity. Kinetic assay was carried out by pipetting aliquots of samples (50 µl) onto 96-well polystyrene plates (Nunc™, Sigma-Aldrich). Reaction was initiated by the addition of 3,3',5,5'-tetramethylbenzidine (TMB) liquid substrate (50 µl, 37° C.). Absorbance measurements were made using a VERSAmax microplate reader (Molecular Devices LLC, Sunnyvale, Calif., USA) at 655 nm. Kinetic rates were recorded every 20 seconds for a total of 10 minutes at 37° C. HRP concentration of the samples was determined by using standard curve as a quantification tool in the range of 0.391 to 200 ng ml$^{-1}$. A standard curve was generated by plotting HRP concentrations of 10 two-fold serial dilutions of HRP solution (200 ng ml$^{-1}$) against their kinetic rates (slope of the absorbance versus time curves).

Statistical Analysis

Mean HRP concentrations with error bars (95% confidence intervals) found in different compartments of gastrointestinal tract were calculated and represented in a graph using IBM SPSS Statistics for Windows, version 22.0.

Results

In the current trial, a fish consumed 12-13 g feed on average during the treatment with feed containing alginate encapsulated HRP. As a result, the treated fish ($m_{avg}$=490–500 g) received between 230 and 240 µg of HRP in the period (Table 3).

TABLE 3

HRP dose related to the fish size in unit of mass and the weekly feed intake (FI) per fish. The dose is shown as a weekly HRP dose per fish (μg fish$^{-1}$ week$^{-1}$) and a weekly HRP dose per unit of fish mass (μg fish$^{-1}$ week$^{-1}$). Feeds used: without HRP (Ctrl-feed), with calcium alginate encapsulated HRP (HRP-Ca-feed), ethylenediammonium alginate encapsulated HRP (HRP-EDA-feed).

| Group | Feed | Fish size (g) ± SD | FI (g fish$^{-1}$ week$^{-1}$) ± SD | HRP dose[i] (μg fish$^{-1}$ week$^{-1}$) ± SD | HRP dose (μg kg$^{-1}$ week$^{-1}$) ± SD |
|---|---|---|---|---|---|
| Control | Ctrl-feed | 492 ± 121 | 12.7 ± 1.7 | 0.00 | 0.00 |
| Ca-alginate | HRP-Ca-feed | 495 ± 95 | 12.5 ± 1.4 | 239 ± 26 | 483 ± 46 |
| EDA-alginate | HRP-EDA-feed | 499 ± 108 | 12.1 ± 0.9 | 232 ± 17 | 465 ± 50 |

[i]HRP dose is theoretical and assumes very little loss due to processing.

The group of fish (Ca-alginate) fed HRP-Ca-feed showed significantly higher concentration of HRP in the distal intestine compared to the other gastrointestinal (GI) compartments (FIG. 3). On the other hand, fish fed HRP-EDA-feed had significantly higher concentration of HRP in the mid intestine than in the other GI sections. Additionally, this group had also notably higher HRP concentration in the distal intestine. In contrast to the HRP treated groups, peroxidase activity was quite low in the control group.

From the FIG. 3, it can be seen that HRP release is significantly faster from EDA-alginate than from Ca-alginate beads. According to the results of the present experiment, it is not expected that drug release from the EDA-alginate is affected by seasonal temperature changes in the habitat of A. salmon. These demonstrated attributes in the present study makes surprisingly an oral delivery system based on EDA-alginate very efficient with respect to fish such as A. salmon.

In conclusion, by way of the present invention it was not only shown that differences do exist between differently cross-linked alginate matrices, but also a novel, more efficient oral delivery systems could be identified. Differences between the EDA-alginate and Ca-alginate are particular evident with respect to dissolution rates at low temperatures. This is highly relevant for ectothermic organisms living at low temperatures such as the Atlantic salmon. In order to recognize these characteristics of alginate beads, the above mentioned new dissolution test strategy has been developed. This new strategy makes the dissolution test highly representative for gastrointestinal conditions found in fish which have a stomach. As a consequence, the results generated by the redesigned dissolution test are in strong correlation with the results obtained from the present in vivo study. On the whole, EDA-alginate is an excellent delivery system for macromolecular drugs to ectothermic animals like salmon. Furthermore, there is convincing evidence that this delivery system is surprisingly temperature-independent within the temperature range of salmon's life habitat. The practical implication of the results of the present study is that the amount of drug delivered is irrespective of the environmental temperature when using this novel oral delivery system.

The advantage of ethylenediammonium alginate micro beads as oral delivery system when incorporated in fish feed and orally administered to fish, is that the beads efficiently dissolve in the fish intestine and deliver the content at the right place for absorbance in the digestive conditions as typically found in fish. However, the present invention, even though being found particularly suitable for use in fish, is not restricted to this group of organisms and may likewise also be used as oral delivery systems for macromolecules in mammals including humans, amphibians, reptiles, birds, crustaceans, molluscs, etc.

Bioactive agent in accordance with the present invention includes any drug, substance, compound, composition or mixture thereof, which are effective in therapy or prophylactic treatment in organisms and which are suitable for encapsulation in alginate and following oral delivery. This includes agents such as proteins, peptides, vaccines, antibodies, antigens, hormones, drugs, particularly macromolecular drugs, amino acids, nucleotides, polynucleotides, enzymes, any physiologically active substance, nutrients, prebiotics, probiotics, immune stimulants and the like.

In the context of the present invention, by the term "cold water" organism is meant any ectothermic animal which typically lives in average environmental temperature of about 20° C. or lower. Likewise a "cold water fish" is a fish living in average water temperatures of about 20° C. or lower. Typical examples for cold water fish are cold water marine fish such as codfish and salmonids.

By the term "short intestinal tract" or "short intestine" in relation to a fish is meant that the total length of the intestine is no more than about 2.5 times the body length of said fish.

It will be appreciated that the features of the invention described in the foregoing can be modified without departing from the scope of the invention as defined in the accompanying claims.

The invention claimed is:

1. A method of therapeutically or prophylactically treating fish, the method comprising:
   administering to the fish an oral delivery system, the oral delivery system comprising a fish feed pellet comprising ethylenediammonium alginate particles having a mean particle size of no more than 2000 microns, the fish feed pellet comprising an oil suspension wherein the ethylenediammonium alginate particles are vacuum coated thereon, the ethylenediammonium alginate particles comprising
   ethylenediammonium alginate; and
   a bioactive agent that is encapsulated or entrapped in the ethylenediammonium alginate;
   wherein the fish is a coldwater fish that lives in average water temperatures of about 20° C. or lower.

2. The method of claim 1, wherein the fish is an omnivorous or carnivorous species.

3. The method of claim 1, wherein the fish is a gastric fish, a fish with a short intestinal tract, salmonids, basses, breams, codfish, halibut, turbot, flounders, grouper, tuna, tilapia, or pangasius.

4. The method of claim 1, wherein the bioactive agent is selected from the group consisting of proteins, peptides, vaccines, antibodies, antigens, hormones, enzymes, immune stimulants, drugs, probiotics, prebiotics, polynucleotides, nucleotides, and amino acids.

5. The method of claim 1, wherein the mean particle size of the ethylenediammonium alginate particles is no more than 300 μm.

6. The method of claim 1, wherein the particles comprise beads.

7. The method of claim 1, wherein the mean particle size of the ethylenediammonium alginate particles is in the range of 300 μm to 2000 μm.

8. The method of claim 1, wherein the mean particle size of the ethylenediammonium alginate particles is no more than 100 μm.

9. The method of claim 1, wherein the mean particle size of the ethylenediammonium alginate particles is no more than 200 μm.

\* \* \* \* \*

UNITED STATES PATENT AND TRADEMARK OFFICE
CERTIFICATE OF CORRECTION

PATENT NO. : 11,844,863 B2
APPLICATION NO. : 17/929556
DATED : December 19, 2023
INVENTOR(S) : Suwan Nalin Jayasinghe et al.

It is certified that error appears in the above-identified patent and that said Letters Patent is hereby corrected as shown below:

On the Title Page

In Column 2, Item (56) under Other Publications, Line 3, delete "?etween" and insert -- between --, therefor Page 2, In Column 1, Item (56) under Foreign Patent Documents, Line 7, delete "W" and insert -- A1 --, therefor.

Page 2, In Column 1, Item (56) under Foreign Patent Documents, Line 8, delete "W" and insert -- A2 --, therefor.

Page 2, In Column 1, Item (56) under Foreign Patent Documents, Line 10, delete "W" and insert -- A2 --, therefor.

Page 2, In Column 1, Item (56) under Other Publications, Line 12, delete "p." and insert -- pp. --, therefor.

Page 2, In Column 2, Item (56) under Other Publications, Line 35, delete "3, No. 8," and insert -- 8, No. 2, --, therefor.

Page 2, In Column 2, Item (56) under Other Publications, Line 37, delete "p." and insert -- pp. --, therefor.

In the Specification

In Column 1, Line 9, delete "PCT/N02016/050113," and insert -- PCT/NO2016/050113, --, therefor.

In Column 5, Line 5, delete "aspect" and insert -- aspect, --, therefor.

In Column 5, Line 57, delete "aspect" and insert -- aspect, --, therefor.

Signed and Sealed this
Eleventh Day of June, 2024

Katherine Kelly Vidal
*Director of the United States Patent and Trademark Office*

CERTIFICATE OF CORRECTION (continued)
U.S. Pat. No. 11,844,863 B2

In Column 6, Line 63, delete "(e.g." and insert -- (e.g., --, therefor.

In Column 8, Line 43, delete "g 1¹" and insert -- g l$^{-1}$ --, therefor.

In Column 8, Line 48, delete "g" and insert -- g l$^{-1}$ --, therefor.

In Column 9, Line 9, delete "(CaCl$_2$) sol. and EDA.2.HCl" and insert -- (CaCl$_2$ sol. and EDA.2HCl --, therefor.

In Column 9, Line 26, delete "CaCl$_2$)" and insert -- CaCl$_2$ --, therefor.

In Column 13, Line 24, delete "CaCl$_2$)" and insert -- CaCl$_2$ --, therefor.